United States Patent [19]  [11] 4,431,672
Yasuda et al.  [45] Feb. 14, 1984

[54] NOVEL 2-(α-SUBSTITUTED ALKYL)-2-IMIDAZOLINE AND PROCESS FOR PRODUCING THE SAME

[75] Inventors: Yutaka Yasuda, Wakayama; Kiyoshi Tsuchihashi, Kainan; Toshiro Nishimura, Wakayama, all of Japan

[73] Assignee: Kao Soap Co., Ltd., Tokyo, Japan

[21] Appl. No.: 317,226

[22] Filed: Nov. 2, 1981

[30] Foreign Application Priority Data

Nov. 10, 1980 [JP] Japan ................................ 55-157838

[51] Int. Cl.³ ........................................... C07D 233/42
[52] U.S. Cl. ..................................................... 424/353
[58] Field of Search ........................................ 548/353

[56] References Cited

U.S. PATENT DOCUMENTS 3,020,276  2/1962  Hughes et al. ....................... 544/333

FOREIGN PATENT DOCUMENTS 191568  3/1967  U.S.S.R. ................................ 548/353

OTHER PUBLICATIONS

Ploog et al., Fette, Seifen, Anstrichmittel 1980, vol. 82, pp. 57–59.

Primary Examiner—Richard Raymond
Attorney, Agent, or Firm—Flynn, Thiel, Boutell & Tanis

[57] ABSTRACT

A 2-(α-substituted alkyl)-2-imidazoline represented by the general formula I:

wherein $R_1$ represents a $C_6$–$C_{20}$ alkyl or alkenyl group and $R_2$ represents a $C_1$–$C_4$ alkyl group which is novel and useful as an intermediate for useful surfactants and polymer-modifiers.

6 Claims, No Drawings

NOVEL 2-(α-SUBSTITUTED ALKYL)-2-IMIDAZOLINE AND PROCESS FOR PRODUCING THE SAME

This invention relates to a novel 2-(α-substituted alkyl)-2-imidazoline represented by the general formula I:

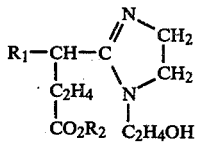

wherein $R_1$ represents a $C_6$–$C_{20}$ alkyl or alkenyl and $R_2$ represents a $C_1$–$C_4$ alkyl, and a process for producing the same.

The reaction of an imidazoline with an alkyl acrylate has heretofore been used as means for producing amidoamine type amphoteric compounds. For example, Jap. Pat. Laid-Open No. 68,721/1978 describes a process wherein an imidazoline is reacted with an alkyl acrylate in the simultaneous presence of water thereby to produce amidoamine type compounds having structures represented by the following general formulas:

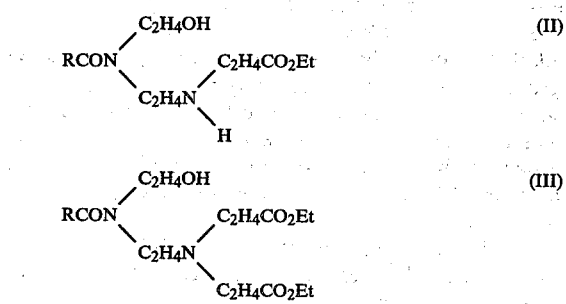

wherein R is an alkyl or an alkenyl.

In this process, amidoamine type compounds are obtained because the imidazoline ring is opened with the water present forming a corresponding amidoamine, to which is then added the alkyl acrylate.

As a result of studies on the reaction of an imidazoline with an alkyl acrylate, the inventors, have found a novel and unique reaction in which, for certain 2-alkyl-2-imidazolines, an alkyl acrylate adds to the α-position of the 2-alkyl group of the imidazoline. As a result of further detailed study of this reaction, the inventors discovered the novel 2-(α-substituted alkyl)-2-imidazolines represented by the general formula I and thereby achieved this invention.

Compounds represented by the general formula I of this invention can be converted into novel carboxylamidoamine type amphoteric compounds which are useful as amphoteric surfactants having a feature that they are mild to the skin, eyes, etc., and the discoloration when stored at high temperatures is little. Thus, compounds represented by the general formula I are important as intermediate compounds for a variety of useful materials.

The invention provides advantageous effects such that the compound of the formula (I) can be converted into a useful compound of the amidoamine type having the formula (VII):

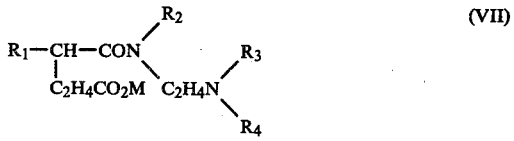

wherein $R_1$ represents a $C_6$–$C_{20}$ alkyl or alkenyl group, $R_2$ represents H or $C_2H_4OH$, $R_3$ and $R_4$ represent each H, $C_2H_4CO_2M$ or $C_2H_4OH$ and when $R_2$ is $C_2H_4OH$, $R_3$ and $R_4$ represent H or $C_2H_4CO_2M$ and when $R_2$ is H, one of $R_3$ and $R_4$ represents $C_2H_4OH$, and M represents H, an alkali metal, an ammonium or an organic ammonium, The compound of the formula (VII) is obtained by adding to the compound of the formula (I), 1.0–5.0 mol of water and optionally an alkyl acrylate in portions, in a total amount not exceeding 5.0 mol; reacting the resulting mixture at a reaction temperature of 40°–90° C.; and saponifying the reaction product with an aqueous alkali solution.

As examples of compounds represented by the general formula I, there can be mentioned 1-(2-hydroxyethyl)-2-(α-methoxycarbonylethylundecyl)-2-imidazoline, 1-(2-hydroxyethyl)-2-(α-ethoxycarbonylethylundecyl)-2-imidazoline, 1-(2-hydroxyethyl)-2-(α-ethoxycarbonyl-ethyloctadecyl)-2-imidazoline, 1-(2-hydroxyethyl)-2-(α-ethoxycarbonylethyloleyl)-2-imidazoline, and 1-(2-hydroxyethyl)-2-(α-ethoxycarbonylethylcoconut alkyl)-2-imidazoline.

The compounds of this invention represented by the general formula I can be produced by the following process which comprises reacting an imidazoline represented by the general formula I-1:

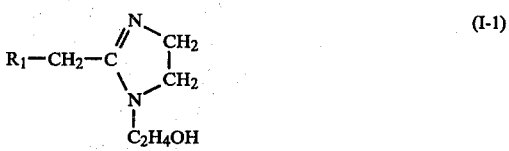

wherein $R_1$ has the same meaning as in the general formula I, with an alkyl acrylate represented by the general formula I-2:

$$CH_2=CH-CO_2R_2 \qquad (I-2)$$

wherein $R_2$ has the same meaning as in the general formula I, under substantially anhydrous conditions.

This process is described in further detail as follows. One mol of an imidazoline represented by the general formula I-1 is mixed with 0.5–10.0 mol, preferably, 1.0–4.0 mol, of an alkyl acrylate. The mixture is reacted without addition of water, in a substantially anhydrous condition at 40°–90° C., preferably 50°–80° C., for 0.5–6 hr., preferably 2–4 hr., and excess unreacted ester is removed by vacuum distillation at a temperature of 20°–80° C., preferably 30°–50° C., thereby producing the novel 2-(α-substituted alkyl)-2-imidazoline represented by the general formula I. This compound showed, owing to the presence of an imidazoline ring, a maximum absorption at 232 mμ on UV spectrum (ethanol solvent) and an absorption at 1605 cm$^{-1}$ on IR spectrum. This compound was decomposed with an alkali and an acid to obtain a fatty acid component. From the results of its acid value and GC-MS spectrum analysis of its methyl ester, this fatty acid component was confirmed to be a dibasic acid represented by the general formula IV:

wherein $R_1$ has the same meaning, as in the general formula I. Consequently, the product compound obtained above was identified as a compound having the structure represented by the general formula I. In this reaction, a small amount of compounds resulting from the addition of the alkyl acrylate to the hydroxyl group of a compound represented by the general formula I or I-1, are also produced as by-products.

The above defined dibasic acid of the formula (IV) can be produced by hydrolyzing the compound of the formula (I) with an alkali or an acid. It is very easy according to the invention to produce the dibasic acid (IV) with a high yield. The dibasic acid (IV) may be converted to an alkali metal, ammonium or an organic ammonium salt thereof, and such salts are useful as emulsifiers, dispersants, and modifiers for polymers such as polyamide and polyester.

The hydrolysis mentioned above may be conducted by (1) preparing a 30% aqueous alkali solution containing an alkyl acrylate and an alkali such as sodium hydroxide or potassium hydroxide at a mole number of 1.0 to 1.5 times said alkyl acrylate; (2) effecting the ring-opening reaction of the imidazoline and saponification of the ester linkage at 40° to 80° C. for 1 to 2 hours; (3) distilling out the resulting alcohol at a reduced pressure; (4) adding an inorganic acid, for example concentrated hydrochloric acid, to the resulting mixture in order to obtain a 2 to 6 N HCL solution thereof; (5) conducting hydrolysis of the amide groups at 90° to 110° C. for 2 to 6 hours; (6) extracting the fatty acid component with ether, and (7) separating the desired dibasic acid of the formula (IV) by distilling out the ether under a reduced pressure.

When the amount of an alkyl acrylate is smaller than 0.5 mol per mol of said imidazoline, the yield of the compound of the general formula I of this invention is lowered. When the amount of an alkyl acrylate is larger than 10 mol per mol of said imidazoline, the amount of unreacted alkyl acrylate increases. This is economically disadvantageous. With respect to the amount of water in the reaction system, the reaction must be carried out in a substantially anhydrous condition.

To conduct the reaction in a substantially anhydrous condition means reacting the starting materials without adding water, although a small amount of water may be present in the starting materials, as a contaminant. A condition in which the reaction system contains less than 0.3% of water is preferred. When the content of water is higher, the yield of the compound of this invention is lowered because of the opening of imidazoline rings.

As the imidazolines of the general formula I-1, used in this invention, there can be mentioned imidazolines which are obtained by dehydration-condensing aminoethylethanolamine with caprylic acid, capric acid, lauric acid, myristic acid, palmitic acid, stearic acid, erucic acid, linoleic acid, coconut oil fatty acid, beef tallow fatty acid or esters thereof. As the alkyl acrylate, there can be mentioned methyl acrylate, ethyl acrylate, propyl acrylate and butyl acrylate.

It is further illustrated below that the imidazolines of the general formula I-1 used in this invention have higher reactivity with an alkyl acrylate, as compared with other imidazoline derivatives.

For example, an alkyl acrylate was reacted with 2-alkyl-2-imidazoline represented by the general formula V:

wherein $R_1$ has the same meaning as in the general formula (I), which was prepared from the fatty acid or an ester thereof and ethylenediamine, or with 1-(2-aminoethyl)-2-alkyl-2-imidazoline represented by the general formula VI:

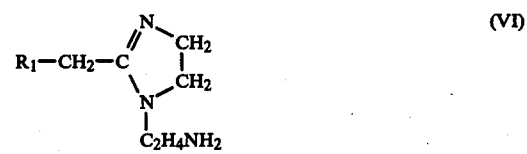

wherein $R_1$ has the same meaning as in the general formula (I), which was prepared from a fatty acid or an ester thereof and diethylenetriamine. As a result of these reactions, it was found that the reactivity of the alkyl acrylate to the α-methylene group of the 2-alkyl group was low, and consequently the yield of 2-(α-substituted alkyl)-2-imidazoline was low in both cases. This indicates that the α-methylene group of the 2-alkyl group of the imidazoline represented by the general formula (I-1) used in this invention has unique high reactivity.

This invention is illustrated below in further detail by examples. In these examples, % means % by weight unless otherwise specified.

EXAMPLE 1

Fifty-three and seven tenths g (53.7 g, 0.2 mol) of 1-(2-hydroxyethyl)-2-undecyl-2-imidazoline was melted, and 60 g (0.6 mol) of ethyl acrylate was added. The mixture was reacted at a temperature of 60°-65° C. for 4 hr. in a substantially anhydrous condition. After the reaction, the excess ethyl acrylate was removed by vacuum-topping the reaction mixture at a temperature of 30°-40° C. Seventy-three and a half g (73.5 g) of 1-(2-hydroxyethyl)-2-(α-ethoxycarbonylethyl-undecyl)-2-imidazoline was obtained as a slightly yellow viscous liquid.

The starting imidazoline and ethyl acrylate used in this example had a water content of 0.02% and a water content of 0.10%, respectively.

This viscous liquid showed a maximum absorption at 232 mμ on UV spectrum measured in ethanol, and showed an absorption due to C=N bond at 1605 cm$^{-1}$ and an absorption due to C=O bond at 1740 cm$^{-1}$. From this fact, the presence of C=N bond in the reaction product, that is, the presence of an imidazoline ring structure, was confirmed.

Moreover, the fatty acid component was converted to its methyl ester, and the ester was then analyzed by GC-MS spectrum method. The mass spectrum of the principal constituent of the fatty acid component was m/e (relative intensity), 269 (19.7, M-31), 236 (13.1, M-64), 227 (8.2, M-73). Accordingly, the structure of this fatty acid methyl ester was confirmed to be

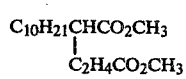

(theoretical molecular weight 300)

Based on these analytical results, the structure of the above viscous liquid was identified. Its purity was 97.0%.

EXAMPLE 2

The reaction was carried out under similar conditions to those used in Example 1, but in this example, the molar ratio of ethyl acrylate to 1-(2-hydroxyethyl)-2-undecyl-2-imidazoline was varied. Table 1 shows the relationship between the molar ratio and the yield of 1-(2-hydroxyethyl)-2-(α-ethoxycarbonylethylundecyl)-2-imidazoline together with the result of Example 1.

TABLE 1

| ethyl acrylate (molar ratio to imidazoline) | yield of 1-(2-hydroxyethyl)-2-(α-ethoxycarbonylethyl-undecyl)-2-imidazoline |
| --- | --- |
| 1.0 | 60.9 |
| 1.5 | 72.2 |
| 2.0 | 90.5 |
| 3.0 | 97.0 |

EXAMPLE 3

This example was carried out in the same manner as in Example 1, except that 57.4 g (0.2 mol) of 1-(2-hydroxyethyl)-2-coconut alkyl-2-imidazoline synthesized from coconut acid (AV 256, average molecular weight 219) and aminoethylethanolamine was used. 1-(2-hydroxyethyl)-2-(α-ethoxycarbonylethyl-coconut alkyl)-2-imidazoline was obtained (yield 95.2%).

EXAMPLE 4

This example was carried out in the same manner as that in Example 1, except that 69.7 g (0.2 mol) of 1-(2-hydroxyethyl)-2-oleyl-2-imidazoline synthesized from oleic acid (AV 200, average molecular weight 280.5) and aminoethylethanolamine was used. 1-(2-hydroxyethyl)-2-(α-ethoxycarbonylethyl-oleyl)-2-imidazoline was obtained (yield 93.8%).

EXAMPLE 5

This example was carried in the same manner as in Example 1, except that 51.6 g (0.6 mol) of methyl acrylate was used. 1-(2-hydroxyethyl)-2-(α-methoxycarbonylethylundecyl)-2-imidazoline was obtained (yield 97.2%).

COMPARATIVE EXAMPLE 1

The reaction was carried out under the same conditions as in Example 1, except that 44.9 g (0.2 mol) of 2-undecyl-2-imidazoline or 53.5 g (0.2 mol) of 1-(2-aminoethyl)-2-undecyl-2-imidazoline was used as the starting imidazoline. Table 2 shows the relationship between each imidazoline and the yield of 2-(α-substituted alkyl)-2-imidazoline, together with the result of Example 1.

TABLE 2

| imidazoline | yield of 2-(α-substituted alkyl)-2-imidazoline (based on imidazoline) |
| --- | --- |
| 2-undecyl-2-imidazoline | 4.2% |
| 1-(2-aminoethyl)-2-undecyl-2-imidazoline | 6.5% |
| 1-(2-hydroxyethyl)-2-undecyl-2-imidazoline | 97.0% |

From Table 2 it is seen that a 2-(α-substituted alkyl)-2-imidazoline derivative can be obtained in a high yield when 1-(2-hydroxyethyl)-2-alkyl-2-imidazoline, which is used in this invention, is used as a starting material.

The embodiments of the invention in which an exclusive property or privilege is claimed are defined as follows:

1. A compound having the formula:

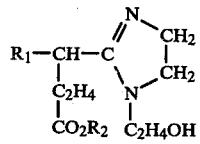

wherein $R_1$ is a $C_6$–$C_{20}$ alkyl or alkenyl and $R_2$ is a $C_1$–$C_4$ alkyl.

2. A compound according to claim 1 which is 1-(2-hydroxyethyl)-2-(α-methoxycarbonylethylundecyl)-2-imidazoline.

3. A compound according to claim 1 which is 1-(2-hydroxyethyl)-2-(α-ethoxycarbonylethylundecyl)-2-imidazoline.

4. A compound according to claim 1 which is 1-(2-hydroxyethyl)-2-(α-ethoxycarbonylethyloctadecyl)-2-imidazoline.

5. A compound according to claim 1 which is 1-(2-hydroxyethyl)-2-(α-ethoxycarbonylethyloleyl)-2-imidazoline.

6. A compound according to claim 1 which is 1-(2-hydroxyethyl)-2-(α-ethoxycarbonylethyl-coconut alkyl)-2-imidazoline.

* * * * *